US00PP33493P2

(12) United States Plant Patent
Meilland

(10) Patent No.: US PP33,493 P2
(45) Date of Patent: Sep. 21, 2021

(54) HYBRID TEA ROSE PLANT NAMED 'MEIROGUSTE'

(50) Latin Name: *Rosa hybrida*
Varietal Denomination: MEIROGUSTE

(71) Applicant: THE CONARD PYLE COMPANY, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/128,315

(22) Filed: Dec. 21, 2020

(30) Foreign Application Priority Data

Sep. 4, 2020 (QZ) ..... PBR 2020/2112

(51) Int. Cl.
*A01H 5/02* (2018.01)
*A01H 6/74* (2018.01)

(52) U.S. Cl.
USPC ..... Plt./133
CPC ..... *A01H 6/749* (2018.05)

(58) Field of Classification Search
USPC ..... Plt./133
CPC ..... A01H 6/749; A01H 5/02
See application file for complete search history.

(56) References Cited

U.S. PATENT DOCUMENTS

PP6,892 P 7/1989 Meilland

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of hybrid tea rose plant, referred to by its cultivar name, 'MEIROGUSTE', is disclosed. The new variety forms on a nearly continuous basis attractive, cup shaped, white colored flowers. Attractive, dense and semi-glossy foliage is formed, which contrasts beautifully with the blossoms. An erected growth habit is displayed. The new variety is well suited for providing attractive ornamentation in the landscape.

1 Drawing Sheet

Botanical/commercial classification:
Latin name: *Rosa hybrida.*
Varietal denomination: 'MEIROGUSTE'.

CROSS-REFERENCE TO RELATED APPLICATIONS

This application claims priority to Plant Breeders' Right Application Number 2020/2112, which was filed at Community Plant Variety Office in the European Union on Sep. 4, 2020, the contents of which are hereby incorporated by reference for all purposes.

SUMMARY OF THE INVENTION

The new variety of *Rosa hybrida* plant was created by artificial pollination wherein two parents were crossed which previously had been studied in the hope that they would contribute the desired characteristics. The female parent (i.e., the seed parent) was the 'TAN99176' variety (non-patented). The male parent (i.e., the pollen parent) was the 'ADAHUIN' variety (non-patented).

The parentage of the new variety can be summarized as follows:

'TAN99176' x 'ADAHUIN'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) emits a strong aniseed fragrance,
(b) forms a white colored flower, and
(c) exhibits a dark green, semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'TAN99176' variety (i.e., the seed parent) displays a climbing growth habit whereas the new variety displays an erected growth habit. The 'ADAHUIN' variety (i.e., the pollen parent) displays red colored flowers, whereas the new variety displays white colored flowers. Moreover, the new variety can be readily distinguished from other similar non-parental varieties. For example, the 'MEIVIOLIN' variety (U.S. Plant Pat. No. 6,892) displays a climbing growth habit compared to the erected growth habit of new variety.

The new variety has been found to undergo asexual propagation in Le Cannet des Maures, Var, France by a number of routes, including softwood cuttings and grafting t-bud. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIROGUSTE'.

The first offer for sale of the new variety was Jun. 29, 2020 in France by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during November while budded on *Rosa Laxa* and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—observe.

Element 8—illustrates a specimen of a fully open flower—plan view—reverse.

Element 9—illustrates a specimen of a fully open flower—plan view—observe.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 5 leaflets—plan view—upper surface.

Element 14—illustrates a specimen of a leaf with 3 leaflets—plan view—upper surface.

Element 15—illustrates a specimen of a leaf with 5 leaflets—plan view—under surface.

Element 16—illustrates a specimen of a leaf with 3 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of one-year-old specimens of the new variety during November while budded on *Rosa Laxa* and growing outdoors at Le Cannet des Maures, Var, France.

Commercial classification: Hybrid Tea Rose Plant.

Plant:

*Habit*.—Erected.

*Height*.—Typically 80 to 150 cm on average.

*Width*.—Typically 50 to 100 cm on average.

Branches:

*Color*.—Young stems: commonly near Green Group 143C. — adult wood: commonly a mix of between near Green Group 143A and near Green Group 143B.

*Length of main stem*.—Approximately 100 cm on average.

*Young shoots*.—Anthocyanin coloration: strong intensity and commonly near Greyed-Purple Group 178A.

*Thorns*.—Configuration on adult stems: concave and elongated on the upper surface and elliptical and narrow on the under surface. — long prickles — quantity: commonly approximately 1 thorn per 10 cm long young stem and commonly 1 thorn per 10 cm long adult stem. — long prickles — base shape: narrow elliptical. — long prickles — size: approximately 0.6 cm in length on average on young stems and adult stems. — long prickles — color: commonly near Greyed-Yellow Group 160B more or less suffused with near Greyed-Purple Group 182A on young stems and commonly near Greyed-Orange Group 165B which evolves to near Greyed-Orange Group 165A towards the point of the thorn on adult stems. — small prickles — quantity: absent.

Foliage:

*General appearance*.—Dense with semi-glossy aspect.

*Number of leaflets*.—3 and 5; most often 5.

*Terminal leaflet*.—Length: approximately 6.5 cm on average. — width: approximately 3.5 cm on average.

*New foliage*.—Upper surface color: commonly a mix between near Yellow-Green Group 146A and Yellow-Green Group 147A, edged with anthocyanin coloration near Greyed-Purple Group 178A. — under surface color: commonly near Green Group 137D with some anthocyanin highlights of near Greyed-Purple Group 178A.

*Adult foliage*.—Upper surface color: commonly a mix between near Green Group 139A and near Yellow-Green Group 147A. — under surface color: commonly near Green Group 137C. — anthocyanin coloration: absent.

Leaflets:

*Shape*.—Tip: acuminate. — base: obtuse.

*Glossiness of upper surface*.—Weak.

*Texture*.—Leathery.

*General appearance*.—Elliptical.

*Edge*.—Slightly denticulate.

*Serration*.—Small and single.

*Undulation on the margin*.—Weak.

*Petiole rachis*.—Color of upper surface: commonly near Green Group 143A. — color of under surface: commonly near Yellow-Green Group 144B.

*Petioles*.—Upper surface: no glandular. — under surface: no prickles. — color of upper surface: commonly near Green Group 143A. — color of under surface: commonly near Yellow-Green Group 144A. — petiole length of terminal leaflet: approximately 2.5 cm on average.

*Stipules*.—General appearance: adnate, pectinate and rather broad. — length: approximately 2.0 cm on average. — width: approximately 0.5 cm on average. — color of upper surface: commonly a mix of between near Yellow-Green Group 144A and near Yellow-Green Group 144B. — color of under surface: commonly a mix of between near Yellow-Green Group 144A and near Yellow-Green Group 144B.

Inflorescence:

*Number of flowers per stem*.—Typically 1 to 10 flowers per stem.

*Lastingness of the bloom*.—On the plant: approximately 8 to 10 days on average.

*Bud*.—Shape: ovoid. — size: medium. — length: approximately 5.0 cm on average. — width: approximately 5.0 cm on average. — color as calyx breaks: upper surface: commonly near Yellow Group 11B edged with near Red-Purple Group 62A, basal spot of near Yellow Group 9A. under surface: commonly near Yellow Group 11C which evolves towards near Red-Purple Group 62D to the edge of the petal.

*Sepals*.—Length: approximately 2.9 cm on average. — width: approximately 0.9 cm on average. — shape: at the top: elongated and narrow, at the base: broad. — extensions: some, weak to medium. — upper surface: texture: tomentous. color: commonly near Yellow-Group 144C with some flat tint of near Green Group 143C. — under surface: texture: smooth. color: commonly near Yellow-Group 144B with some flat tint of near Green Group 143B.

*Receptacle*.—Color: commonly a mix between near Green Group 143B and Green Group 143C. — length: approximately 1.0 cm on average. — width: approximately 1.0 cm on average. — surface: smooth. — shape: funnel shaped.

*Peduncle*.—Length: approximately 3.5 cm on average. — width: approximately 0.4 cm on average. — surface: smooth. — color: commonly a mix between near Green Group 143B and Green Group 143C.

*Flower*.—Average size when fully open: approximately 12 cm on average. — shape: cup shaped. — type: double. — number of petals under normal conditions: typically 60 to 105 petals on average. — shape of the petal: base: pointed. top: rounded slightly cordiform. — texture of the petal: soft. — petal length: approximately 5.0 cm on average. — petal width: approximately 6.0 cm on average. — petal arrangement: imbricated without petaloids. — petal drop: petals drop off cleanly before drying. — fragrance: strong aniseed fragrance. — color when opening: — basal spot: commonly near Yellow Group 9C. upper surface of the flower: commonly near Yellow-White Group 158D edged with near Red-Purple Group 62C. under surface of the flower: commonly near Yellow-White Group 158D. — color of the open flower: basal spot: commonly near Yellow Group 9C. upper surface of the flower: commonly near Yellow-White Group 158D edged with near Red-Purple Group 62D. under surface of the flower: commonly near Yellow-White Group 158D. — anthers: number is approximately 120 on average, length is approximately 0.3 cm on average, coloration is commonly near Yellow-Orange Group 21B, and arrangement is regular around styles. — filaments: length is approximately 1.0 cm on average and coloration is commonly near Yellow-Orange Group 17C. — styles: length is approximately 0.5 cm on average, coloration is commonly near Green-White Group 157D, and number is approximately 155 on average. — stigmas: size is approximately 0.1 cm on average and coloration is commonly near Yellow Group 6C with highlights near Orange Group 29C. — pollen: color is commonly near Yellow Group 8B and amount is abundant. — hips: not available at this stage.

Development:

*Vegetation*.—Strong.

*Blooming*.—Early in the season, abundant and nearly continuous, typical from May to November in France.

*Usda hardiness zone*.—Zone 5.

*Tolerance to disease*.—Good, and particularly against downy mildew (*Peronospora sparsa*) and powdery mildew (*Odium*).

The new 'MEIROGUSTE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIROGUSTE' characterized by the following combination of characteristics:

(a) emits a strong aniseed fragrance, (b) forms a white colored flower, and (c) exhibits a dark green, semi-glossy foliage;

substantially as herein shown and described.

* * * * *

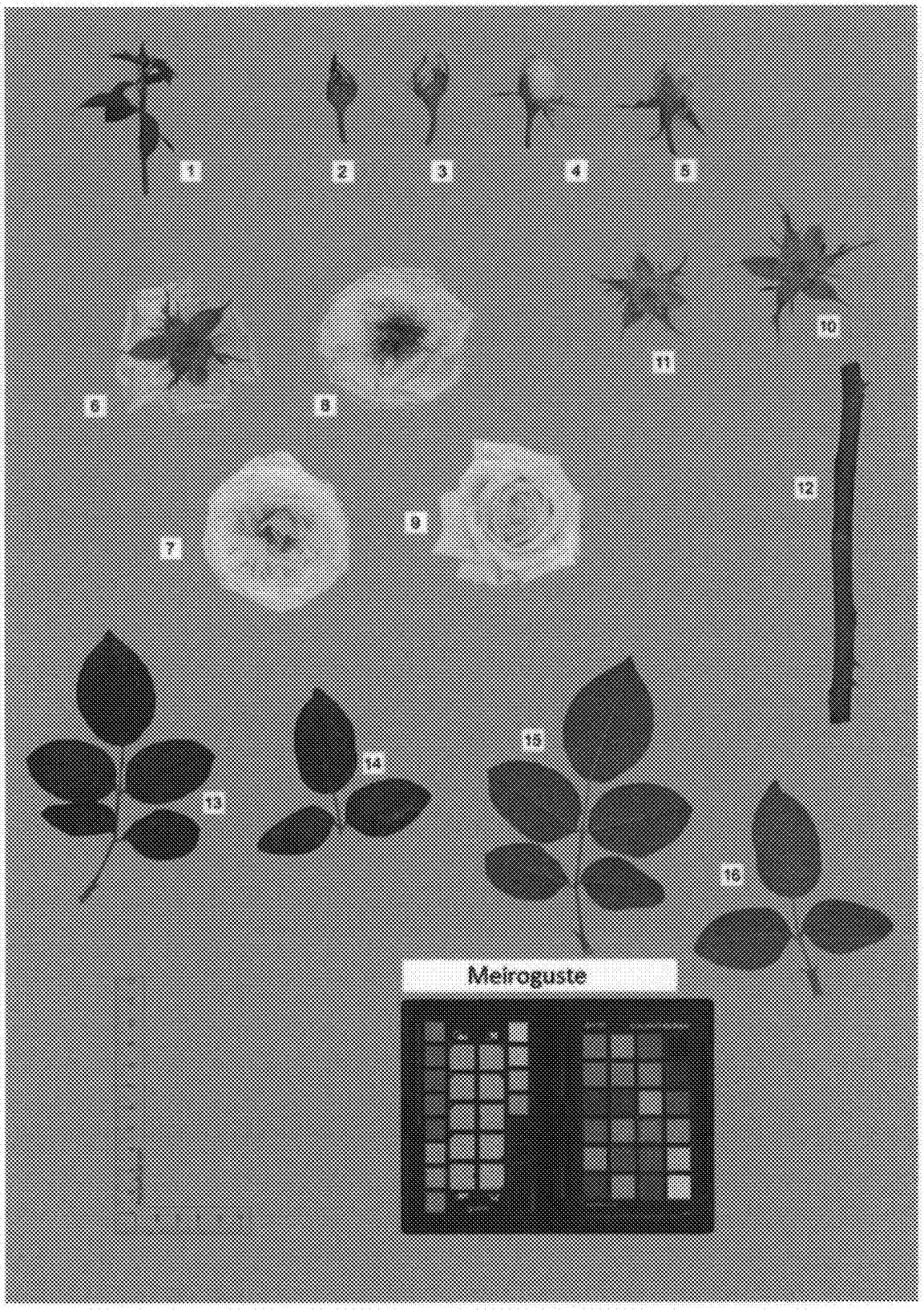
1
2
3
4
5
6
7
8
9
10
11
12
13
14
15
Meiroguste